Figure 1:
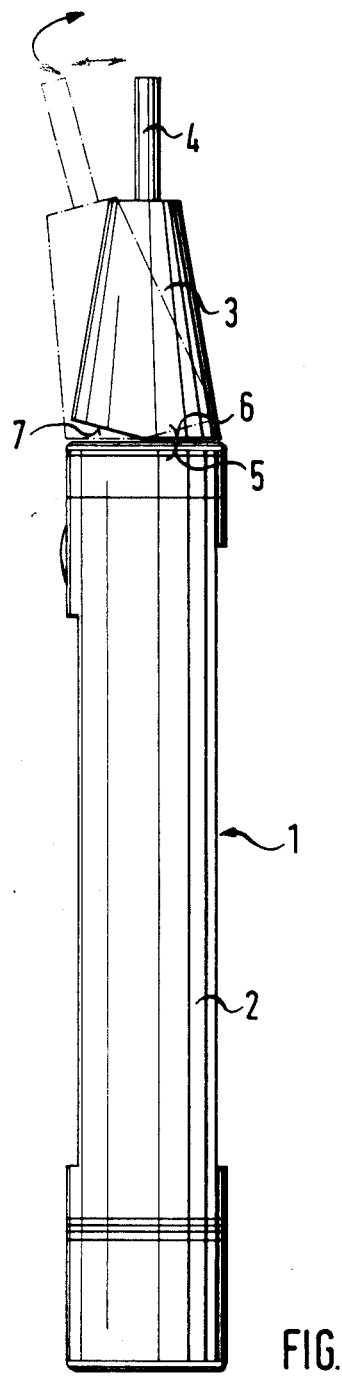

United States Patent [19]

Hommann

[11] Patent Number: 4,974,278
[45] Date of Patent: Dec. 4, 1990

[54] ELECTRIC TOOTHBRUSH
[75] Inventor: Edgar Hommann, Grossaffoltern, Switzerland
[73] Assignee: Gimelli & Co. AG, Switzerland
[21] Appl. No.: 306,200
[22] Filed: Feb. 6, 1989
[30] Foreign Application Priority Data
   Feb. 6, 1988 [DE] Fed. Rep. of Germany ....... 3803646
[51] Int. Cl.⁵ .................. A46B 13/02; F16H 21/00
[52] U.S. Cl. ................................. 15/22 R; 74/23
[58] Field of Search .......................... 15/22 R; 74/23
[56] References Cited
   U.S. PATENT DOCUMENTS
   3,533,119  10/1970  Dokos ............................ 15/22 R
   4,756,202  7/1988   Kawamoto ....................... 15/22 R FOREIGN PATENT DOCUMENTS
   2838015  3/1979  Fed. Rep. of Germany ..... 15/22 R Primary Examiner—Edward L. Roberts
Attorney, Agent, or Firm—Wegner, Cantor, Mueller & Player

[57] ABSTRACT

An electric toothbrush has a gear driven by a motor. On the face of the gear is an eccentric pin upon which a sliding member is located. The eccentric pin engages with a socket in a lever which is securely connected to a brush rod. The lever is moved up and down and simultaneously oscillates due to the rotational movement of the eccentric pin so that the brush rod executes a corresponding movement.

19 Claims, 5 Drawing Sheets

ELECTRIC TOOTHBRUSH

BACKGROUND OF THE INVENTION

The invention relates to an electric toothbrush which has a brush rod housed in the toothbrush casing in such a way to be rotatable, the brush rod being rotatable around its longitudinal axis by an electric motor with a rotating motor shaft by means of an eccentric pin which engages with a lever, the lever being securely fixed to the brush rod. Such an electric toothbrush is in general familiar and conventional.

The rotary motion of the motor is converted, in the familiar toothbrushes, into an oscillatory movement of the brush rod by means of a lever which is transversely aligned to the brush rod and which engages with an eccentric pin aligned parallel to the brush rod. Thus, a brush element placed on the brush rod moves in oscillatory motion accordingly. Recently this simple movement of the brush element has often been considered insufficient and a demand for a circling movement has arisen. For this movement, the brush rod must not only accomplish an oscillatory movement around its longitudinal axis but must also be moved simultaneously backwards and forwards in a lengthwise direction. To produce both of these superposed movements, relatively complicated gearing has been provided for the familiar toothbrushes up to the present so that the production of this sort of toothbrush is on the whole expensive.

The object of the invention is to construct a toothbrush of the type named at the beginning so that the rotary motion of its motor may be converted, with the most simple gearing as possible, into a simultaneous oscillatory and backwards and forwards movement.

The object is achieved in accordance with the invention in that the brush rod is, in addition, arranged so as to be slidable in axial direction and that the lever is axially parallel to the brush rod and the eccentric pin is perpendicular to the brush rod the eccentric pin gripping into a socket in the lever, the socket being in transverse direction to the brush rod.

This construction allows the eccentric cam to push the lever backwards and forwards with the brush rod, in the direction of the brush rod so that the desired axial shift of the brush rods takes place. Simultaneously, the eccentric cam causes on oscillatory movement of the lever to one side or the other when it moves in its orbit towards the sides. In this way, the two desired and superposed movements of the brush rod are achieved by means of a simple crank mechanism. Owing to the invention a very simple and therefore, reasonably priced toothbrush may be produced, the brush elements of which performing a circular movement which is advantageous for thorough cleaning of the teeth.

It is of particularly great advantage if a sliding member is positioned on the eccentric pin so as to be rotatable, the sliding member engaging with the socket and if both sides of the sliding member running axially parallel to the brush rod, and/or the corresponding sides of the socket, are curved or bevelled to enable an oscillatory movement of the lever. Such an arrangement operates with very little friction and may be produced at a reasonable price.

To enable the oscillatory movement of the lever, either the sides of the sliding member are convex or the sides of the socket in the lever, in contact with the sliding member, are concave. It is of course also possible for each of the contacting areas to be curved.

The toothbrush is structurally especially simple, in accordance with one advantageous embodiment of the invention, if the eccentric pin is provided on the face of a gear, this being transversely rotatable to the brush rod and housed in the toothbrush casing, whereby on the motor shaft, a pinion engages with the gear. The gear may, for example, be a bevel gear or a crown wheel. It is simply important that the motor shaft has a bell-crank drive so that the axis of the eccentric pin runs in transverse direction to the motor shaft and thus, in transverse direction to the brush rod.

The oscillatory movement of the lever is especially simple to produce, in accordance with another embodiment of the invention, if the part of the lever with the socket for the sliding member is of radial distance from the brush rod. This embodiment has a sliding member which engages with the lever at a considerable distance from the oscillatory axis of the lever, the oscillatory axis of the lever being the same as that of the brush rod. This results in a relatively great oscillatory momentum so that the oscillatory movement of the brush element occurs with great enough force.

Another embodiment is very space-saving if, according to this embodiment, the eccentric pin engages with the sliding member from the side of the brush rod.

Manually operated dental instruments are normally bent at the point where the handle begins. The brush element of an electric toothbrush may also have this bent form if, according to a further development of the invention, the gear is arranged in a front part of the toothbrush which bears the brush rod, the front part being rotatable and tiltable by means of a ball head and positioned in a ball cup in the handle of the toothbrush casing, the handle housing the motor. The centre of the ball head lies at the point of intersection of the gear axle and the motor shaft axle.

The gear allows for tilting of the front part of the toothbrush when necessary only around the gear axle due to the pinion engaging with the gear. To exclude forces on the gear and on the pinion, in an attempt to tilt the front part of the toothbrush into another direction, it is advantageous if the front part of the toothbrush has a support at each side of the axle which bears the gear, the support being in contact with a collar at the front of the handle. These supports prevent tilting into directions other than a direction transverse to the gear axle.

The possible direction of tilt of the front part of the toothbrush is clearly fixed if, according to another embodiment of the invention, the front part of the toothbrush is in contact with the collar at the front of the handle with a support area covering 180 degrees and if its tiltability is restricted by an inclined area adjoining this support area.

Another, very simple possibility of preventing the front part of the toothbrush from tilting into a direction which is not transverse to the gear axle is achieved when the gear axle protrudes out of the ball head on at least one side and engages with a bow-shaped groove in the handle.

The invention permits numerous embodiments. To clarify the basic principle of the invention further, an embodiment of the latter is represented in drawing and subsequently described.

Figure 2:
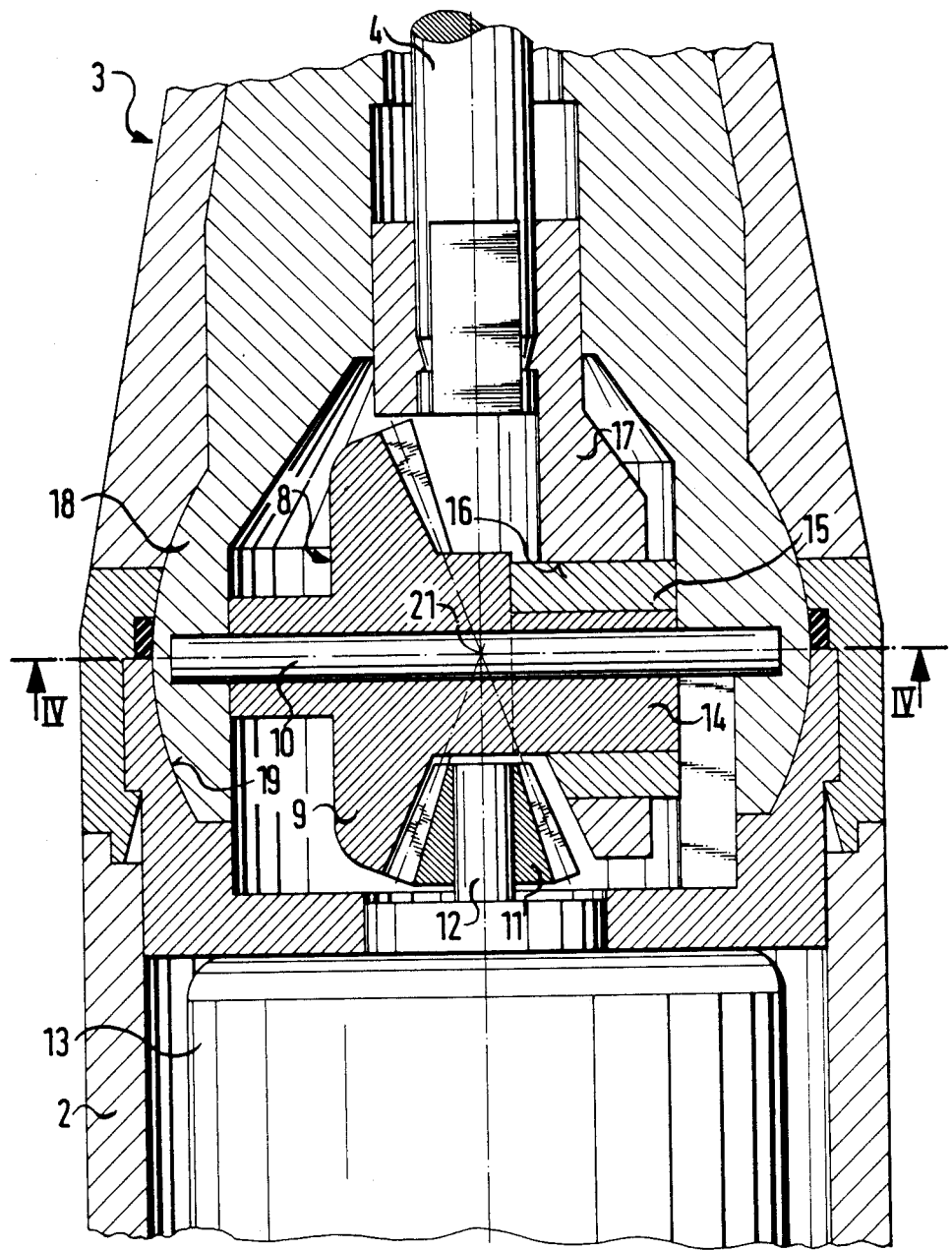
Figure 3:
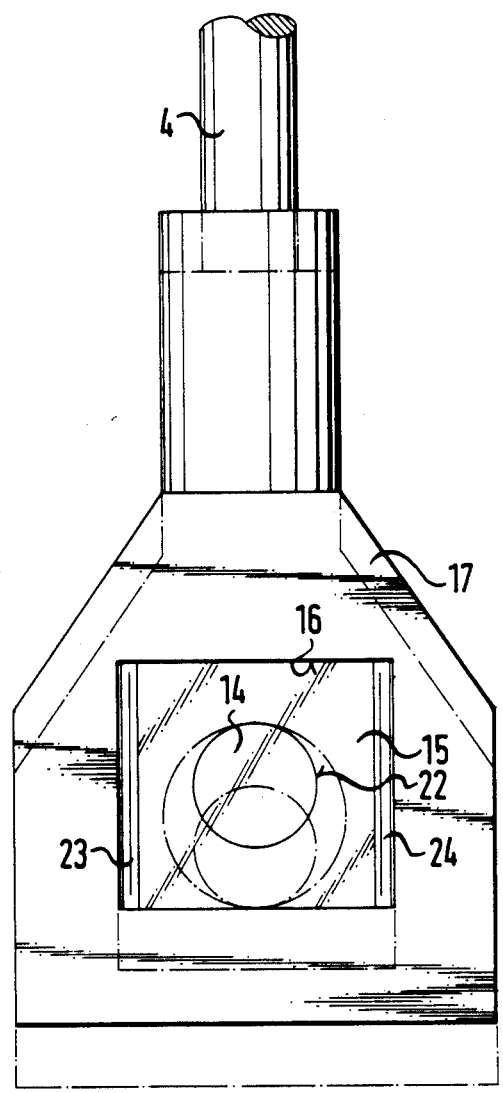
Figure 4:
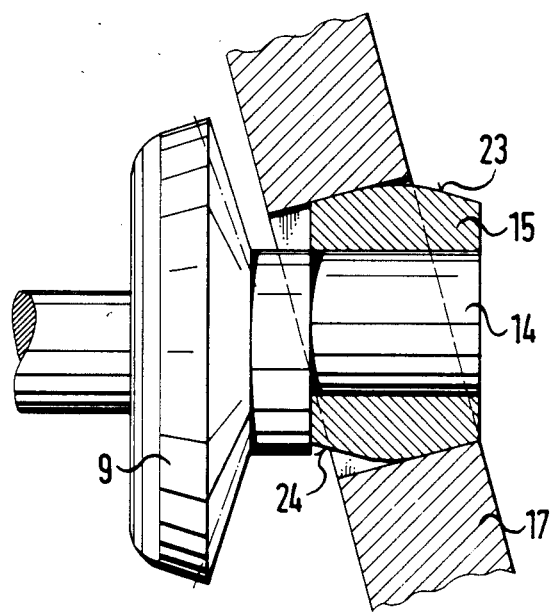
Figure 5:
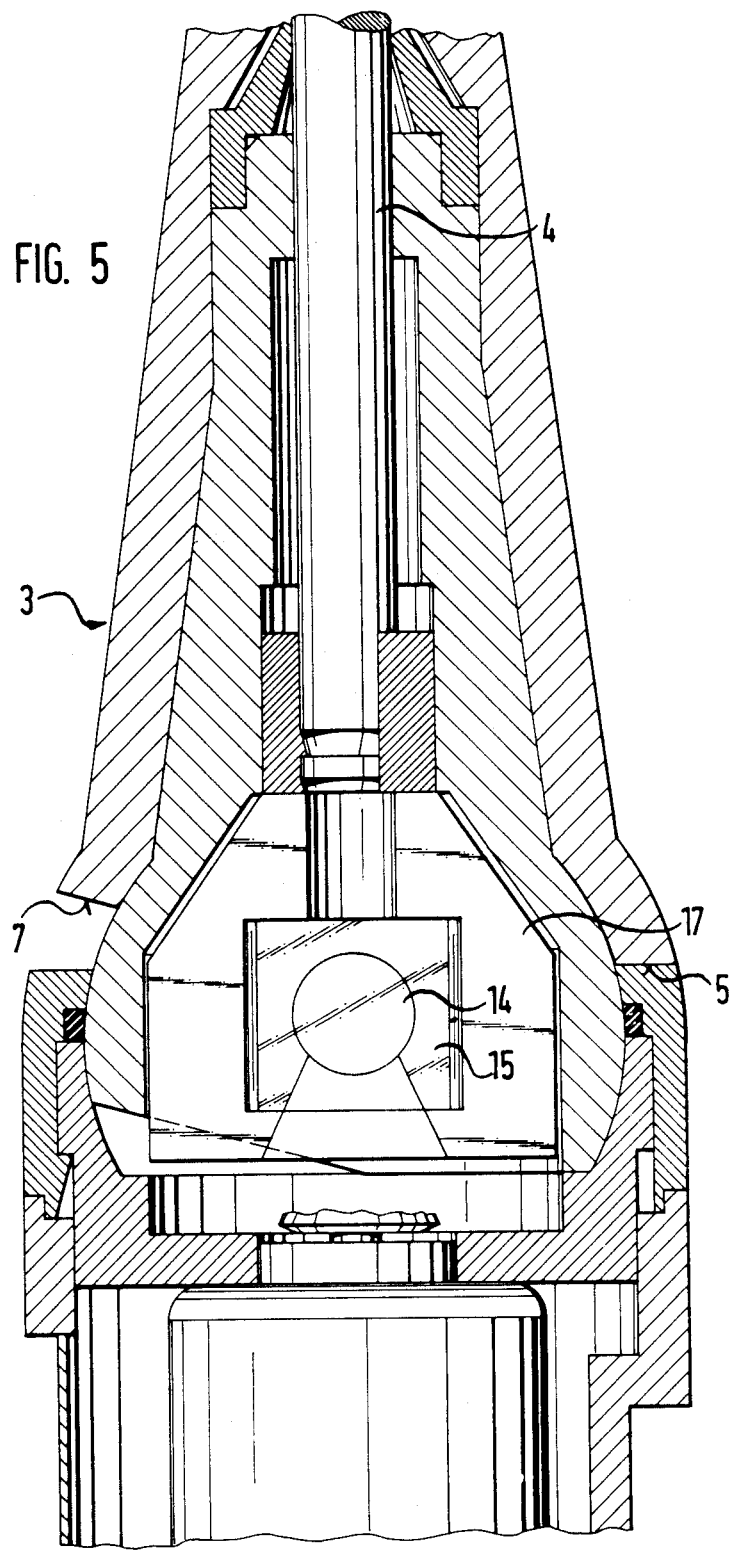

FIG. 1 is a view of a toothbrush constructed according to the invention,

FIG. 2 is a longitudinal section through the gearing area of the toothbrush according to FIG. 1, FIG. 3 is a side of a lever in the toothbrush with neighbouring components, FIG. 4 is a partial cross section through the toothbrush without its casing along the line IV—IV in FIG. 2, FIG. 5 is a longitudinal section through the toothbrush according to FIG. 1 and in respect of FIG. 2 has been rotated through 90 degrees.

Figure 6:
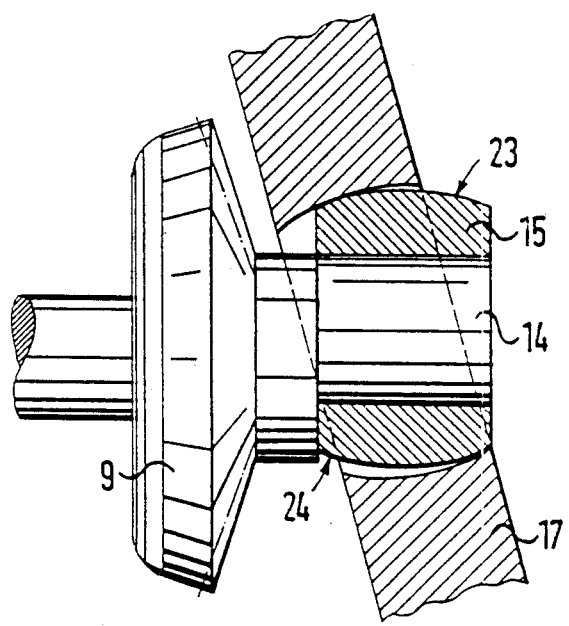

FIG. 6 is a partial cross section through the toothbrush without its casing along the line IV—IV in FIG. 2 according to another embodiment of the invention.

The toothbrush represented as a whole in FIG. 1 has a casing 1 which consists essentially of a handle 2 and a front part 3 out of which a brush rod 4 protrudes. When the toothbrush is in use, a brush element, (not shown), is placed on this protruding part of the brush rod 4.

As may be seen in FIG. 1, the front part 3 of the toothbrush is mounted with a support 5 on a collar 6 at the front of the handle 2..The support 5 adjoins an inclined area 7 on the front part 3 of the toothbrush. Thus, it is possible to tilt the front part 3 of the toothbrush out of the position represented in unbroken lines in the drawing so far to the left until the position represented in dots and dashes is reached and the inclined area 7 rests on the collar 6 of the handle 2, the support 5 being instead directed away from the collar 6 at an angle.

Apart from being able to tilt the front part 3 of the toothbrush, it is also possible to turn the latter with its brush rod 4 around the longitudinal axis of the toothbrush. Both possible movements are clarified in FIG. 1 by arrows.

FIG. 2 clarifies in particular the construction of a gearing 8 which enables movement of the front part 3 of the toothbrush. The gearing 8 has a gear 9 which is borne in the front part 3 of the toothbrush by an axle 10. This axle 10 runs transversely to the brush rod 4. The gear 9 is driven by a pinion 11 which is arranged coaxially to the brush rod 4 and is located on a motor shaft 12 of an electric motor 13.

Towards one face, the gear 9 has an eccentric pin 14 which is consequently also aligned transverse to the brush rod 4. A sliding member 15 is arranged on this eccentric pin 14 and is held so as to be unrotatable in a socket 16 of a lever 17. This lever 17 is fixed to the brush rod 4 so as to be movable therewith. The lever 17 is formed so that the socket 16 is laterally displaced from the axis of the brush rod 4. The lever 17 moves up and down due to the movement of the sliding member 15 caused by the circular movements of eccentric 14. The lever 17 also oscillates simultaneously with the up-and-down movement. The exact sequence of motion becomes clearer with the following figures.

To be seen further in FIG. 2 is that the front part 3 of the toothbrush engages with a ball head 18 in a ball cup 19 of the handle 2. By means of this construction the front part 3 of the toothbrush may be turned around the longitudinal axis of the toothbrush. In addition, the front part 3 of the toothbrush is tiltable in transverse direction to the plane of the drawing. For this tilting movement it is important that the centre line of the axle 10 intersects the centre line of the motor shaft 12 and that this intersection, positioned at 21 in the drawing, is simultaneously the centre of the ball head 18 and the ball cup 19.

As shown in FIG. 3, the socket 16 of the lever 17 is held on the brush rod 4 in such a manner that it may only rotate with the brush rod 4. The socket 16 is rectangular in cross section and the sliding member 15 is correspondingly rectangular. This sliding member 15 has a hole 22 in which the eccentric pin 14 engages. If the eccentric pin 14 turns through 180 degrees and thus, reaches its lower position represented in dots and dashes, the lever 17 moves correspondingly downwards so that the brush rod 4 shifts in an axial direction. Since the eccentric pin 14 is in its intermediate position, (not shown), to the side of the axis of the brush rod 4, the lever 17 should actually shift to the side as well. This movement, however, is impossible because the brush rod 4 is mounted so as to prevent lateral movement thereof. Instead of moving sideways, the lever 17 makes a oscillatory movement, which is caused by the bow-shaped side areas 23, 24 of the sliding member 15 and by the lateral displacement of the sliding member 15 from the axis of the brush rod 4. Thus, oscillatory momentum is created when the sliding member 15 in its socket 16 moves the lever 17 so that the lever 17 rotates around the axis of the brush rod 4 and therefore moves the brush rod 4 correspondingly.

FIG. 4 clarifies that the side areas 23, 24 of the sliding member 15 are sloped in a bow-shape. Thus, the lever 17 may occupy the rotated position when the eccentric pin 14 is in its represented position and with respect to FIG. 3 a position shifted through 90 degrees, so that the lever 17 does not move to the side.

FIG. 5 shows the inclined area 7 and the support area 5 of the front of the toothbrush already mentioned in FIG. 1. To be noticed further in FIG. 5, located on the brush rod 4 is the lever 17 which is, moved up and down and in addition, moved in oscillatory motion around its longitudinal axis by means of the sliding member 15. Also to be seen in FIG. 5 is the eccentric pin 14 which engages with the sliding member 15. Not shown, however, are the gear 9 and its axle 10 since these components lie, seen in respect of FIG. 5, behind the lever 17.

What is claimed is:

1. Electric toothbrush comprising:
   a tooth brush casing;
   a brush rod mounted in the toothbrush casing so as to be rotatably and longitudinally movable;
   a lever fixed to said brush rod, wherein said lever has a socket portion which is provided with a socket having a center axis perpendicular to the longitudinal axis of the brush rod;
   an eccentric cam which communicates with said socket, wherein said eccentric cam has a rotational axis which is perpendicular to the longitudinal axis of the brush rod; and
   means for rotating said eccentric cam to cause an oscillatory movement of the lever and the brush rod about the longitudinal axis of the brush rod and a longitudinal movement of the lever and the brush rod along the longitudinal axis of the brush rod.

2. Electric toothbrush as claimed in claim 1 wherein said socket has a substantially rectangular shape, said electric toothbrush further comprising a substantially rectangular sliding member disposed within said socket and rotatably connected to said eccentric cam, wherein sides of said sliding member which are parallel to the longitudinal axis of the brush rod are bow-shaped.

3. Electric toothbrush as claimed in claim 2, wherein said socket portion of said lever is laterally displaced from the longitudinal axis of the brush rod.

4. Electric toothbrush as claimed in claim 3, wherein said eccentric cam engages the sliding member from a side of the sliding member nearer the brush rod.

5. Electric toothbrush as claimed in claim 1 wherein said socket has a substantially rectangular shape, said electric toothbrush further comprising a substantially rectangular sliding member disposed within said socket and rotatably connected to said eccentric cam, wherein sides of said socket which are parallel to the longitudinal axis of the brush rod are bow-shaped.

6. Electric toothbrush as claimed in claim 5, wherein said socket portion of said lever is laterally displaced from the longitudinal axis of the brush rod.

7. Electric toothbrush as claimed in claim 6, wherein said eccentric cam engages the sliding member from a side of the sliding member nearer the brush rod.

8. Electric toothbrush as claimed in claim 1 wherein said socket has a substantially rectangular shape, said electric toothbrush further comprising a substantially rectangular sliding member disposed within said socket and rotatably connected to said eccentric cam, wherein sides of said socket which are parallel to the longitudinal axis of the brush rod and sides of said sliding member which are parallel to the longitudinal axis of the brush rod are bow-shaped.

9. Electric toothbrush as claimed in claim 8, wherein said socket portion of said lever is laterally displaced from the longitudinal axis of the brush rod.

10. Electric toothbrush as claimed in claim 9, wherein said eccentric cam engages the sliding member from a side of the sliding member nearer the brush rod.

11. Electric toothbrush as claimed in claim 1, wherein said means for rotating said eccentric cam comprises:
a motor having a rotatable motor shaft;
a pinion gear disposed at the distal end of the rotatable motor shaft; and
rotatable gear means mechanically engaged with said pinion gear, wherein said eccentric cam is fixed to said rotatable gear means.

12. Electric toothbrush as claimed in claim 11, wherein the rotational axis of the rotatable motor shaft is parallel to the longitudinal axis of the brush rod, and wherein the rotational axis of the rotatable gear means is perpendicular to the longitudinal axis of the brush rod.

13. Electric toothbrush as claimed in claim 1, wherein the toothbrush casing comprises a front section and a handle section, and wherein said front section is rotatable and tiltable with respect to the handle portion.

14. Electric toothbrush as claimed in claim 13, wherein said means for rotating said eccentric cam comprises:
a motor having a rotatable motor shaft;
a pinion gear disposed at the distal end of the rotatable motor shaft; and
rotatable gear means mechanically engaged with said pinion gear, wherein said eccentric cam is fixed to said rotatable gear means.

15. Electric toothbrush as claimed in claim 14, wherein the rotational axis of the rotatable motor shaft is parallel to the longitudinal axis of the brush rod, and wherein the rotational axis of the rotatable gear means is perpendicular to the longitudinal axis of the brush rod.

16. Electric toothbrush as claimed in claim 15, wherein the front section comprises a ball head positioned in a ball cup provided on the handle portion, wherein the brush rod, the lever, the eccentric cam and the rotatable gear means are disposed within the front section, wherein the motor is disposed within the handle section, and wherein the center of the ball head lies at the point of intersection of the rotational axis of the rotatable motor shaft and the rotational axis of the rotatable gear means.

17. Electric toothbrush as claimed in claim 13, wherein said rotatable gear means comprises a gear rotatably mounted on an axle, wherein said axle is supported at the ends thereof by support means, and wherein said support means is in contact with a collar disposed on an end of the handle portion adjacent the front portion.

18. Electric toothbrush as claimed in claim 17, wherein one half of an end of the front section adjacent the handle section is in contact with said collar, and wherein the other half of the end of the front section is inclined away from the collar.

19. Electric toothbrush as claimed in claim 17, wherein at least one end of said axle protrudes out of the ball head, and wherein said support means comprises at least one bow-shaped groove in the handle section.

* * * * *